United States Patent
Mahler et al.

(10) Patent No.: US 8,692,037 B2
(45) Date of Patent: *Apr. 8, 2014

(54) COMPOSITIONS COMPRISING 1,1,1,2,3-PENTAFLUOROPROPANE OR 2,3,3,3-TETRAFLUOROPROPENE

(71) Applicant: E I du Pont de Nemours and Company, Wilmington, DE (US)

(72) Inventors: Barry Asher Mahler, Glen Mills, PA (US); Mario Joseph Nappa, Newark, DE (US); Jeffrey P Knapp, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/676,217

(22) Filed: Nov. 14, 2012

(65) Prior Publication Data

US 2013/0068989 A1 Mar. 21, 2013

Related U.S. Application Data

(62) Division of application No. 13/408,686, filed on Feb. 29, 2012, now Pat. No. 8,333,902, which is a division of application No. 12/437,014, filed on May 7, 2009, now Pat. No. 8,147,709.

(60) Provisional application No. 61/126,813, filed on May 7, 2008.

(51) Int. Cl.
*C07C 21/185* (2006.01)

(52) U.S. Cl.
USPC .......................... 570/136; 252/67

(58) Field of Classification Search
USPC ........................... 570/136; 252/67
See application file for complete search history.

(56) References Cited

U.S. PATENT DOCUMENTS

| 4,560,759 A | 12/1985 | Hiratani |
| 4,902,838 A | 2/1990 | Manzer et al. |

(Continued)

FOREIGN PATENT DOCUMENTS

| DE | 20 2007 088 291 U1 | 10/2007 |
| EP | 2 028 172 A1 | 2/2009 |

(Continued)

OTHER PUBLICATIONS

PCT Partial International Search Report, Aug. 10, 2009.

(Continued)

*Primary Examiner* — John Hardee

(57) ABSTRACT

Disclosed are compositions comprising HFC-245eb and at least one additional compound selected from the group consisting of HFO-1234ze, HFC-245fa, HFC-236cb, HFC-236ea, HFC-236fa, HFC-227ea, HFC-227ca, HFO-1225yc, HFO-1225zc, HFO-1225ye, methane, ethane, propane, HFC-23, HFC-143a, HFC-134, HFC-134a, FC-1216, HFO-1234yf, HFC-254eb, HFO-1243zf, and HFC-254fb. Compositions comprising HFC-245eb are useful in processes to make HFO-1234yf. Also disclosed are compositions comprising HFO-1234yf and at least one additional compound selected from the group consisting of HFO-1234ze, HFC-254eb, HFC-254fb, HFO-1243zf, HFCHFC-245eb, HFC-245fa, HFC-245cb, HFC-236cb, HFC-236ea, HFC-236fa, HFC-227ea, HFC-227ca, HFO-1225yc, HFO-1225zc, HFO-1225ye, methane, ethane, propane, HFC-23, HFC-134, HFC-134a, HFO-1132a and FC-1216. Compositions comprising HFO-1234yf are useful as heat transfer compositions for use in refrigeration, air-conditioning and heat pump systems.

2 Claims, 1 Drawing Sheet

(56) References Cited

U.S. PATENT DOCUMENTS

| | | |
|---|---|---|
| 4,978,649 A | 12/1990 | Surovikin et al. |
| 5,136,113 A | 8/1992 | Rao |
| 5,268,122 A | 12/1993 | Rao et al. |
| 5,396,000 A | 3/1995 | Nappa et al. |
| 5,616,275 A | 4/1997 | Chisolm et al. |
| 5,800,729 A | 9/1998 | Wilson et al. |
| 5,954,995 A | 9/1999 | Goble |
| 6,369,284 B1 | 4/2002 | Nappa et al. |
| RE37,938 E | 12/2002 | Minor et al. |
| 6,548,719 B1 | 4/2003 | Nair et al. |
| 7,230,146 B2 | 6/2007 | Merkel et al. |
| 7,335,804 B2 | 2/2008 | Nair et al. |
| 7,641,809 B2 | 1/2010 | Leck et al. |
| 7,695,595 B2 | 4/2010 | Balthasart et al. |
| 8,147,709 B2 | 4/2012 | Mahler et al. |
| 2002/0003224 A1 | 1/2002 | Hughes et al. |
| 2005/0211949 A1 | 9/2005 | Bivens et al. |
| 2005/0233932 A1 | 10/2005 | Singh et al. |
| 2006/0179852 A1 | 8/2006 | Thomas et al. |
| 2006/0243944 A1 | 11/2006 | Minor et al. |
| 2006/0243945 A1 | 11/2006 | Minor et al. |
| 2007/0100175 A1 | 5/2007 | Miller et al. |
| 2007/0112230 A1 | 5/2007 | Mukhopadhyay et al. |
| 2007/0179324 A1 | 8/2007 | Van Der Puy et al. |
| 2007/0197842 A1 | 8/2007 | Mukhopadhyay et al. |
| 2008/0058562 A1 | 3/2008 | Petrov et al. |
| 2008/0207962 A1 | 8/2008 | Rao et al. |
| 2008/0207963 A1 | 8/2008 | Rao et al. |
| 2008/0207964 A1 | 8/2008 | Rao et al. |
| 2010/0090156 A1 | 4/2010 | Nappa et al. |
| 2011/0031436 A1 | 2/2011 | Mahler et al. |

FOREIGN PATENT DOCUMENTS

| | | |
|---|---|---|
| GB | 2 439 392 A | 12/2007 |
| GB | 2 440 258 A | 1/2008 |
| JP | 4110388 A | 4/1992 |
| RU | 2073058 C1 | 2/1997 |
| WO | 01/32323 A1 | 5/2001 |
| WO | 2007/117391 A1 | 10/2007 |
| WO | 2007/145171 A1 | 12/2007 |
| WO | 2008/002499 A2 | 1/2008 |
| WO | 2008/002500 A1 | 1/2008 |
| WO | 2008/009928 A2 | 1/2008 |
| WO | 2008/030439 A2 | 3/2008 |
| WO | 2008030439 A2 | 3/2008 |
| WO | 2008030440 A2 | 3/2008 |
| WO | 2008/054778 A2 | 5/2008 |
| WO | 2008/054779 A1 | 5/2008 |
| WO | 2008/054780 A2 | 5/2008 |
| WO | 2008/060614 A1 | 5/2008 |
| WO | 2008054781 A1 | 5/2008 |
| WO | 2008054782 A1 | 5/2008 |
| WO | 2008/076272 A2 | 6/2008 |
| WO | 2008/079265 A1 | 7/2008 |
| WO | 2011/087825 A1 | 7/2011 |

OTHER PUBLICATIONS

PCT International Search Report, Oct. 9, 2009.

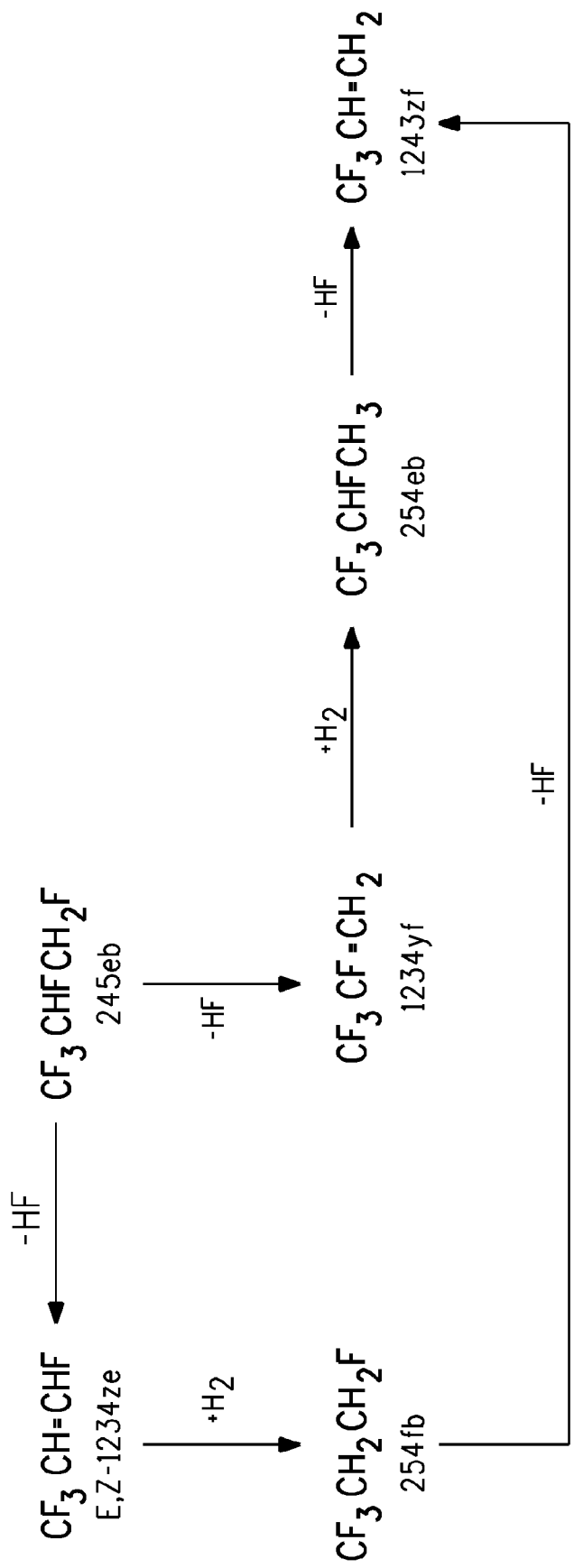

COMPOSITIONS COMPRISING 1,1,1,2,3-PENTAFLUOROPROPANE OR 2,3,3,3-TETRAFLUOROPROPENE

CROSS REFERENCE TO RELATED APPLICATIONS

This application is a division of allowed U.S. application Ser. No. 13/408,686, now U.S. Pat. No. 8,333,902, filed Feb. 29, 2012 which claims priority to granted U.S. Pat. No. 8,147,709 (Ser. No. 12/437,014, filed May 7, 2009), which claims the priority benefit of U.S. Provisional Application No. 61/126,813, filed May 7, 2008.

BACKGROUND

1. Field of the Invention

The present disclosure relates to the field of compositions which may be useful as heat transfer compositions, aerosol propellants, foaming agents, blowing agents, solvents, cleaning agents, carrier fluids, displacement drying agents, buffing abrasion agents, polymerization media, expansion agents for polyolefins and polyurethane, gaseous dielectrics, extinguishing agents, and fire suppression agents in liquid or gaseous form. In particular, the present disclosure relates to compositions which may be useful as heat transfer compositions, such as 2,3,3,3-tetrafluoropropene (HFO-1234yf, or 1234yf) or the compositions comprising 1,1,1,2,3-pentafluoropropane (HFC-245eb, or 245eb) which are useful in processes to produce HFO-1234yf.

2. Description of Related Art

New environmental regulations have led to the need for new compositions for use in refrigeration, air-conditioning and heat pump apparatus. Low global warming potential compounds are of particular interest.

SUMMARY OF THE INVENTION

Applicants have found that in preparing such new low global warming potential compounds, such as HFO-1234yf, that certain additional compounds are present in small amounts.

Therefore, in accordance with the present invention, there is provided a composition comprising HFO-1234yf and at least one additional compound selected from the group consisting of HFO-1234ze, HFC-254eb, HFC-254fb, HFO-1243zf, HFC-245eb, HFC-245fa, HFC-245cb, HFC-236cb, HFC-236ea, HFC-236fa, HFC-227ea, HFC-227ca, HFO-1225yc, HFO-1225zc, HFO-1225ye, 3,3,3-trifluoropropyne, methane, ethane, propane, HFC-23, HFC-143a, HFC-134, HFC-134a, HFO-1132a, and FC-1216. The composition contains less than about 1 weight percent of the at least one additional compound.

In addition, in accordance with the present invention, there is provided a composition comprising HFC-245eb and at least one additional compound selected from the group consisting of HFO-1234ze, HFC-245fa, HFC-245ca, HFC-236cb, HFC-236ea, HFC-236fa, HFC-227ea, HFC-227ca, HFO-1225yc, HFO-1225zc, HFO-1225ye, methane, ethane, propane, HFC-23, HFC-143a, HFC-134, HFC-134a, FC-1216, HFO-1234yf, HFC-254eb, HFO-1243zf, and HFC-254fb. In this case, the composition may contain anywhere from greater than zero weight percent to about 99 weight percent of HFC-245eb. The compositions comprising HFC-245eb are useful in processes to produce HFO-1234yf.

BRIEF DESCRIPTION OF THE DRAWING

FIG. 1 is a schematic drawing showing a reaction for producing HFO-1234yf from HFC-245eb, and the side reactions from HFO-1234yf and HFC-245eb that may simultaneously occur during the HFC-245eb to HFO-1234yf reaction step.

DETAILED DESCRIPTION OF THE PREFERRED EMBODIMENTS

In one embodiment, the present disclosure provides a composition comprising HFC-245eb and at least one additional compound selected from the group consisting of HFO-1234ze, HFC-245fa, HFC-236cb, HFC-236ea, HFC-236fa, HFC-227ea, HFC-227ca, HFO-1225yc, HFO-1225zc, HFO-1225ye, methane, ethane, propane, HFC-23, HFC-143a, HFC-134, HFC-134a, FC-1216, HFO-1234yf, HFC-254eb, HFO-1243zf, and HFC-254fb.

In one embodiment, the total amount of additional compound(s) in the composition comprising HFC-245eb ranges from greater than zero weight percent to about 99 weight percent. In another embodiment, the total amount of additional compounds ranges from about 1 weight percent to about 80 weight percent. In another embodiment, the total amount of additional compound(s) ranges from about 1 weight percent to about 50 weight percent. In another embodiment, the total amount of additional compound(s) ranges from about 1 weight percent to about 30 weight percent. In another embodiment, the total amount of additional compound(s) ranges from about 1 weight percent to about 10 weight percent.

In some embodiments, certain precursor compounds to HFC-245eb contain impurities that appear in the HFC-245eb. In other embodiments, the additional compounds are formed by reaction of these precursor impurities. In other embodiments, the reaction conditions under which the HFC-245eb is produced also produce by-products, by which is meant alternative reaction pathways may produce additional compounds depending upon the particular conditions under which the HFC-245eb is produced.

In another embodiment, the present disclosure provides a composition comprising HFO-1234yf and at least one additional compound selected from the group consisting of HFO-1234ze, HFC-254eb, HFC-254fb, HFO-1243zf, HFC-245eb, HFC-245fa, HFC-245cb, HFC-236cb, HFC-236ea, HFC-236fa, HFC-227ea, HFC-227ca, HFO-1225yc, HFO-1225zc, HFO-1225ye, 3,3,3-trifluoropropyne, methane, ethane, propane, HFC-23, HFC-143a, HFC-134, HFC-134a, HFO-1132a, and FC-1216.

In one embodiment, the total amount of additional compound(s) in the composition comprising HFO-1234yf ranges from greater than zero weight percent to less than 1 weight percent.

In some embodiments, the impurities present in the HFC-245eb will remain intact during the reaction to make HFO-1234yf. Thus they are included in the additional compounds.

The compositions comprising HFC-245eb are useful in processes to produce HFO-1234yf.

The compositions disclosed herein comprising HFO-1234yf are useful as heat transfer compositions, aerosol propellants, foaming agents, blowing agents, solvents, cleaning agents, carrier fluids, displacement drying agents, buffing abrasion agents, polymerization media, expansion agents for polyolefins and polyurethane, gaseous dielectrics, extinguishing agents, and fire suppression agents in liquid or gaseous form. The disclosed compositions can act as a working fluid used to carry heat from a heat source to a heat sink. Such heat transfer compositions may also be useful as a refrigerant in a cycle wherein the fluid undergoes a phase change; that is, from a liquid to a gas and back or vice versa.

Examples of heat transfer systems include but are not limited to air conditioners, freezers, refrigerators, heat pumps, water chillers, flooded evaporator chillers, direct expansion chillers, centrifugal chillers, walk-in coolers, heat pumps, mobile refrigerators, mobile air conditioning units and combinations thereof.

As used herein, mobile refrigeration apparatus, mobile air conditioning or mobile heating apparatus refers to any refrigeration, air conditioner, or heating apparatus incorporated into a transportation unit for the road, rail, sea or air. In addition, mobile refrigeration or air conditioner units, include those apparatus that are independent of any moving carrier and are known as "intermodal" systems. Such intermodal systems include "containers" (combined sea/land transport) as well as "swap bodies" (combined road/rail transport).

As used herein, stationary heat transfer systems are systems contained within or attached to buildings of any variety. These stationary applications may be stationary air conditioning and heat pumps (including but not limited to chillers (including centrifugal chillers), high temperature heat pumps, residential, commercial or industrial air conditioning systems, and including window, ductless, ducted, packaged terminal, and those exterior but connected to the building such as rooftop systems). In stationary refrigeration applications, the disclosed compositions may be useful in equipment including commercial, industrial or residential refrigerators and freezers, ice machines, self-contained coolers and freezers, flooded evaporator chillers, direct expansion chillers, walk-in and reach-in coolers and freezers, and combination systems. In some embodiments, the disclosed compositions may be used in supermarket refrigerator systems.

The compounds making up the disclosed compositions are defined in Table 1.

TABLE 1

| Code | Structure | Chemical name |
|---|---|---|
| HFC-245eb | $CF_3CHFCH_2F$ | 1,1,1,2,3-pentafluoropropane |
| HFO-1234yf | $CF_3CF=CH_2$ | 2,3,3,3-tetrafluoropropene |
| HFO-1234ze | $CF_3CH=CHF$ | E- or Z-1,3,3,3-tetrafluoropropene |
| HFC-245fa | $CF_3CH_2CHF_2$ | 1,1,1,3,3-pentafluoropropane |
| HFC-236cb | $CF_3CF_2CH_2F$ | 1,1,1,2,2,3-hexafluoropropane |
| HFC-236ea | $CF_3CHFCHF_2$ | 1,1,1,2,3,3-hexafluoropropane |
| HFC-236fa | $CF_3CH_2CF_3$ | 1,1,1,3,3,3-hexafluoropropane |
| HFC-227ea | $CF_3CHFCF_3$ | 1,1,1,2,3,3,3-heptafluoropropane |
| HFC-227ca | $CF_3CF_2CHF_2$ | 1,1,1,2,2,3,3-heptafluoropropane |
| HFO-1225yc | $CF_2HCF=CF_2$ | 1,1,2,3,3-pentafluoropropene |
| HFO-1225zc | $CF_3CH=CF_2$ | 1,1,1,3,3-pentafluoropropene |
| HFO-1225ye | $CF_3CF=CHF$ | 1,2,3,3,3-pentafluoropropene |
| | $CF_3C\equiv CH$ | 3,3,3-trifluoropropyne, |
| HFC-23 | $CHF_3$ | trifluoromethane |
| HFC-143a | $CF_3CH_3$ | 1,1,1-trifluoroethane |
| HFC-134 | $CHF_2CHF_2$ | 1,1,2,2-tetrafluoroethane |
| HFC-134a | $CF_3CH2F$ | 1,1,1,2-tetrafluoroethane |
| FC-1216 | $CF_3CF=CF_2$ | hexafluoropropene (HFP) |
| HFC-254eb | $CF_3CHFCH_3$ | 1,1,1,2-tetrafluoropropane |
| HFC-254fb | $CF_3CH_2CH_2F$ | 1,1,1,3-tetrafluoropropane |
| HFO-1243zf | $CF_3CH=CH_2$ | 1,1,1-trifluoropropene (TFP) |
| HFO-1132a | $CH_2=CF_2$ | 1,1-difluoroethene |

HFC-245eb is available from specialty chemical manufacturers, including SynQuest Laboratories, Inc. of Alachua, Fla., or it may be made by methods known in the art. One series of steps that can be used to produce HFC-245eb starts with hexafluoropropene (HFP). HFP may be hydrogenated to produce 1,1,1,2,3,3-hexafluoropropane (HFC-236ea). Then HFC-236ea may be dehydrofluorinated to produce 1,2,3,3,3-pentafluoropropene (HFC-1225ye). HFC-1225ye may be hydrogenated yielding the desired HFC-245eb. The hydrogenation steps may, for example, be conducted as described in PCT Publication No. WO2008/030440. The dehydrofluorination of HFC-236ea to HFO-1225ye may, for example, be conducted under the same conditions as described herein for HFC-245eb dehydrofluorination to HFO-1234yf.

The other compounds of Table 1 may be available commercially, or may be prepared as known in the art.

Of the compounds of Table 1 those that will be present in the disclosed compositions will depend upon the method of manufacture.

In some embodiments, certain precursor compounds to HFC-245eb contain impurities that then appear as additional compounds in the HFC-245eb compositions. In other embodiments, these precursor compounds may themselves react during the HFC-245eb formation to produce additional compounds that then appear in the HFC-245eb compositions. In other embodiments, the reaction conditions under which the HFC-245eb is produced also produce by-products, by which is meant adventitious reaction pathways may occur simultaneously to produce compounds other than HFC-245eb and the quantity and identity of these additional compounds will depend upon the particular conditions under which the HFC-245eb is produced.

In some embodiments, HFO-1234yf is made by dehydrofluorination of HFC-245eb. This reaction is shown in FIG. 1.

Catalytic Dehydrofluorination

In one embodiment, the dehydrofluorination is carried out in the vapor phase using a dehydrofluorination catalyst. Dehydrofluorination catalysts include but are not limited to alumina, aluminum fluoride, fluorided alumina, metal compounds on aluminum fluoride, metal compounds on fluorided alumina; oxides, fluorides, and oxyfluorides of magnesium, zinc and mixtures of magnesium and zinc and/or aluminum; lanthanum oxide and fluorided lanthanum oxide; chromium oxides, fluorided chromium oxides, and cubic chromium trifluoride; carbon, acid washed carbon, activated carbon, three dimensional matrix carbonaceous materials; and metal compounds supported on carbon. The metal compounds may be oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof.

In one embodiment, the catalytic vapor phase dehydrofluorination of HFC-245eb is carried out using fluorided alumina, aluminum fluoride or mixtures thereof as catalysts in a manner analogous to the dehydrofluorination of HFC-236ea to HFO-1225ye as disclosed in U.S. Pat. No. 5,396,000. Fluorided alumina and aluminum fluoride can be prepared as described in U.S. Pat. No. 4,902,838, or by treatment of alumina with a vaporizable fluorine containing compound such as $CF_2Cl_2$, $CF_2HCl$, and $CHF_3$.

In other embodiments, the dehydrofluorination of HFC-245eb is carried out using carbon, activated carbon, or three dimensional matrix carbonaceous materials as catalysts in a manner analogous to the processes disclosed in U.S. Pat. No. 6,369,284; or using metals such as sodium, potassium, rubidium, cesium, yttrium, lanthanum, cerium, praseodymium, neodymium, samarium, chromium, iron, cobalt, rhodium, nickel, copper, zinc, and mixtures thereof, supported on carbon as catalysts in a manner analogous to the processes disclosed in U.S. Pat. No. 5,268,122. Carbon from any of the following sources are useful for the dehydrofluorination: wood, peat, coal, coconut shells, bones, lignite, petroleum-based residues and sugar. Commercially available carbons which may be used include those sold under the following trademarks: Barneby & Sutcliffe™, Darco™, Nucharm™, Columbia JXN™ Columbia LCK™, Calgon PCB™, Calgon BPL™, Westvaco™, Norit™, and Barnaby Cheny NB™.

Carbon includes acid-washed carbon (e.g., carbon that has been treated with hydrochloric acid or hydrochloric acid followed by hydrofluoric acid). Acid treatment is typically sufficient to provide carbon that contains less than 1000 ppm of ash. Suitable acid treatment of carbon is described in U.S. Pat. No. 5,136,113. The carbon also includes three dimensional matrix porous carbonaceous materials. Examples are those described in U.S. Pat. No. 4,978,649. Of note are three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

In a further embodiment, the catalytic dehydrofluorination of HFC-245eb is carried out using chromium oxides, fluorided chromium oxides, and cubic chromium trifluoride as catalysts. Cubic chromium trifluoride may be prepared from $CrF_3 \cdot XH_2O$, where X is 3 to 9, preferably 4, by heating in air or an inert atmosphere (e.g., nitrogen or argon) at a temperature of about 350° C. to about 400° C. for 3 to 12 hours, preferably 3 to 6 hours.

The physical shape of the catalyst is not critical and may, for example, include pellets, powders or granules. Additionally, for catalysts supported on carbon, the carbon may be in the form of powder, granules, or pellets, or the like. Although not essential, catalysts may be treated with HF before use. It is thought that this converts some of the surface oxides to oxyfluorides. This pretreatment can be accomplished by placing the catalyst in a suitable container (which can be the reactor to be used to perform the reaction) and thereafter, passing HF over the dried catalyst so as to partially saturate the catalyst with HF. This is conveniently carried out by passing HF over the catalyst for a period of time (e.g., about 15 to 300 minutes) at a temperature of, for example, about 200° C. to about 450° C.

The catalytic dehydrofluorination may be suitably conducted at a temperature in the range of from about 200° C. to about 500° C., and is preferably conducted at a temperature in the range of from about 300° C. to about 450° C. The contact time is typically from about 1 to about 450 seconds, preferably from about 10 to about 120 seconds.

The reaction pressure can be subatmospheric, atmospheric or superatmostpheric. Generally, near atmospheric pressures are preferred. However, the dehydrofluorination can be beneficially run under reduced pressure (i.e., pressures less than one atmosphere).

The catalytic dehydrofluorination can optionally be carried out in the presence of an inert gas such as nitrogen, helium, or argon. The addition of an inert gas can be used to increase the extent of dehydrofluorination. Of note are processes where the mole ratio of inert gas to hydrofluorocarbon undergoing dehydrofluorination is from about 5:1 to about 0.5:1. Nitrogen is the preferred inert gas.

Pyrolysis (Thermal Dehydrofluorination)

In one embodiment, the dehydrofluorination of HFC-245eb to produce HFO-1234yf may be carried out by the pyrolysis of HFC-245eb. The reaction may be written as:

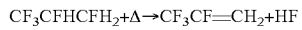

where Δ represents heat, and HF is hydrogen fluoride.

HFC-245eb can be prepared by the hydrogenation of $CF_3CClFCCl_2F$ (CFC-215bb) over a palladium on carbon catalyst as disclosed in International Application No. PCT/US07/14646, filed Jun. 22, 2007 and published as WO2008/002501 on Jan. 3, 2008, or by the hydrogenation of $CF_3CF=CFH$ as disclosed in U.S. Pat. No. 5,396,000.

Pyrolysis, as the term is used herein, means chemical change produced by heating in the absence of catalyst. Pyrolysis reactors generally comprise three zones: a) a preheat zone, in which reactants are brought close to the reaction temperature; b) a reaction zone, in which reactants reach reaction temperature and are at least partially pyrolyzed, and products and any byproducts form; c) a quench zone, in which the stream exiting the reaction zone is cooled to stop the pyrolysis reaction. Laboratory-scale reactors have a reaction zone, but the preheating and quenching zones may be omitted.

The reactor for carrying out the pyrolysis may be of any shape consistent with the process but is preferably a cylindrical tube, either straight or coiled. Although not critical, such reactors typically have an inner diameter of from about 1.3 to about 5.1 cm (about 0.5 to about 2 inches). Heat is applied to the outside of the tube, the chemical reaction taking place on the inside of the tube. The reactor and its associated feed lines, effluent lines and associated units should be constructed, at least as regards the surfaces exposed to the reactants and products, of materials resistant to hydrogen fluoride. Typical materials of construction include stainless steels, in particular of the austenitic type, the well-known high nickel alloys, such as nickel-copper alloys commercially available from Special Metals Corp. (New Hartford, N.Y.) under the trademark Monel®, nickel-based alloys commercially available from Haynes International (Kokomo, Ind.) under the trademark Hastelloy® (hereinafter referred to as "Hastelloy®") and nickel-chromium alloys commercially available from Special Metals Corp. under the trademark Inconel®, and copper-clad steel.

Where the reactor is exposed to high temperature the reactor may be constructed of more than one material. For example, the outer surface layer of the reactor should be chosen for ability to maintain structural integrity and resist corrosion at the pyrolysis temperature, the inner surface layer of the reactor should be chosen of materials resistant to attack by, that is, inert to, the reactant and products. In the case of the present process, the product hydrogen fluoride is corrosive to certain materials. Thus, the reactor may be constructed of an outer material chosen for physical strength at high temperature and an inner material chosen for resistance to corrosion by the reactants and products under the temperature of the pyrolysis.

In one embodiment, the reactor inner surface layer is made of high nickel alloy, that is an alloy containing at least about 50 wt % nickel, preferably a nickel alloy having at least about 75 wt % nickel, more preferably a nickel alloy having less than about 8 wt % chromium, still more preferably a nickel alloy having at least about 98 wt % nickel, and most preferably substantially pure nickel, such as the commercial grade known as Nickel 200. More preferable than nickel or its alloys as the material for the inner surface layer of the reactor is gold. The thickness of the inner surface layer does not substantially affect the pyrolysis and is not critical so long as the integrity of the inner surface layer is intact. The thickness of the inner surface layer is typically from about 10 to about 100 mils (0.25 to 2.5 mm). The thickness of the inner surface layer can be determined by the method of fabrication, the cost of materials, and the desired reactor life.

In one embodiment, the reactor outer surface layer is resistant to oxidation or other corrosion and maintains sufficient strength at the reaction temperatures to keep the reaction vessel from failing of distorting. In one embodiment, this layer is a nickel, iron, chromium alloy sold by Special Metals Corp. (New Hartford, N.Y.) under the trademark Inconel®. In another embodiment, this layer is another nickel, iron, chromium alloy sold by Special Metals Corp. under the trademark Inconel® 600.

The pyrolysis of HFC-245eb to HFO-1234yf and HF is carried out in the absence of catalyst in a substantially empty reactor. By absence of catalyst is meant that no material or treatment is added to the pyrolysis reactor that increases the reaction rate by reducing the activation energy of the pyrolysis process. It is understood that although surfaces that are unavoidably present in any containment vessel, such as a pyrolysis reactor, may have incidental catalytic or anticatalytic effects on the pyrolysis process, the effect makes an insignificant contribution, if any, to the pyrolysis rate. More specifically, absence of catalyst means absence of conventional catalysts in a particulate, pellet, fibrous or supported form that are useful in promoting the elimination of hydrogen fluoride from a hydrofluorocarbon (i.e., dehydrofluorination). Examples of such dehydrofluorination catalysts include: fluorided alumina, aluminum fluoride, chromium oxide, optionally containing other metals, metal oxides or metal halides; chromium fluoride, and activated carbon, optionally containing other metals, metal oxides or metal halides, and others as listed previously herein.

In one embodiment, substantially empty reactors useful for carrying out the dehydrofluorination are tubes comprising the aforementioned materials of construction. Substantially empty reactors include those wherein the flow of gases through the reactor is partially obstructed to cause back-mixing, i.e. turbulence, and thereby promote mixing of gases and good heat transfer. This partial obstruction can be conveniently obtained by placing packing within the interior of the reactor, filling its cross-section or by using perforated baffles. The reactor packing can be particulate or fibrillar, preferably in cartridge disposition for ease of insertion and removal, has an open structure like that of Raschig rings (ceramic or metal pieces of tube that are approximately equal in length and diameter) or other packings with a high free volume, to avoid the accumulation of coke and to minimize pressure drop, and permits the free flow of gas. Preferably the exterior surface of such reactor packing comprises materials identical to those of the reactor inner surface layer; materials that do not catalyze dehydrofluorination of hydrofluorocarbons and are resistant to hydrogen fluoride. The free volume of the reaction zone is at least about 80%, preferably at least about 90%, and more preferably about 95%. The free volume is the volume of the reaction zone minus the volume of the material that makes up the reactor packing.

In one embodiment, the pyrolysis which accomplishes the conversion of HFC-245eb to HFO-1234yf is suitably conducted at a temperature of from about 450° C. to about 900° C. In another embodiment, the pyrolysis is conducted at a temperature of from about 550° C. to about 850° C. In another embodiment, the pyrolysis is conducted at a temperature of from about 600° C. to about 750° C. The pyrolysis temperature is the temperature of the gases inside the reaction zone at about the mid-.

In one embodiment, the residence time of gases in the reaction zone is from about 0.5 to about 60 seconds. In another embodiment, the residence time is from about 2 seconds to about 20 seconds.

In one embodiment, the pyrolysis can be conducted in the presence of one or more unreactive diluent gases, that is diluent gases that do not react under the pyrolysis conditions. Such unreactive diluent gases include the inert gases nitrogen, argon, and helium. Fluorocarbons that are stable under the pyrolysis conditions, for example, trifluoromethane and perfluorocarbons, may also be used as unreactive diluent gases. Of note are processes where the mole ratio of inert gas to HFC-245eb fed to the pyrolysis reactor is from about 5:1 to 1:1. Nitrogen is a preferred inert gas because of its comparatively low cost.

In one embodiment, the pyrolysis reaction is conducted at subatmospheric total pressure. In another embodiment, the pyrolysis reaction can be beneficially run under reduced total pressure (i.e., total pressure less than one atmosphere). In another embodiment, the pyrolysis reaction is carried out at or near atmospheric total pressure.

Liquid Phase Dehydrofluorination

In one embodiment, the dehydrofluorination of HFC-245eb is accomplished using an aqueous alkaline solution. In one embodiment, the reaction is carried out in the presence of a non-aqueous solvent in which the HFC-245eb ($CF_3CHFCH_2F$) is at least partially miscible. In another embodiment, the reaction is carried out with no non-aqueous solvent. In another embodiment, the reaction is carried out in the presence of a phase transfer catalyst. In yet another embodiment, the reaction is carried out with no phase transfer catalyst.

In one embodiment, the base in the aqueous alkaline solution is selected from the group consisting of hydroxide, oxide, carbonate, or phosphate salts of alkali metals, alkaline earth metals, and mixtures thereof. In one embodiment, bases which may be used include without limitation lithium hydroxide, sodium hydroxide, potassium hydroxide, calcium hydroxide, magnesium oxide, calcium oxide, sodium carbonate, potassium carbonate, sodium phosphate, potassium phosphate, or the like and mixtures thereof.

As used herein, the aqueous alkaline solution is a liquid (whether a solution, dispersion, emulsion, or suspension and the like) that is primarily an aqueous liquid having a pH of over 7. In some embodiments the basic aqueous solution has a pH of over 8. In some embodiments, the basic aqueous solution has a pH of over 10. In some embodiments, the basic aqueous solution has a pH of 10-13. In some embodiments, the basic aqueous solution contains small amounts of organic liquids which may be miscible or immiscible with water. In some embodiments, the liquid medium in the aqueous alkaline solution is at least 90% water. In one embodiment the water is tap water; in other embodiments the water is deionized or distilled water.

The amount of base (in the aqueous alkaline solution) required to convert HFC-245eb to HFO-1234yf is approximately the stoichiometric quantity or about 1 mole of base to one mole of HFC-245eb. In one embodiment, it may desirable (e.g., to increase reaction rate) to employ a ratio of base to HFC-245eb of greater than one. In some embodiments, large excesses of base (in the basic aqueous solution) are to be avoided as further reaction of the desired hydrofluoroolefin may occur. Thus, in some embodiments, it may be necessary to employ an amount of base (in the basic aqueous solution) that is slightly below the stoichiometric amount so as to minimize secondary reactions. Thus, in one embodiment, the molar ratio of base (in the basic aqueous solution) to HFC-245eb is from about 0.75:1 to about 10:1. In another embodiment, the molar ratio of base (in the basic aqueous solution) to HFC-245eb is from about 0.9:1 to about 5:1. In yet another embodiment, the molar ratio of base to HFC-245eb is from about 1:1 to about 4:1.

In certain embodiments, the non-aqueous solvent is selected from the group consisting of alkyl and aryl nitriles, alkyl and aryl ethers, alcohols, amides, ketones, sulfoxides, phosphate esters and mixtures thereof.

In one embodiment, a solid base (e.g., KOH, NaOH, LiOH or mixtures thereof) is dissolved in water, or alternatively, a concentrated solution of a base (e.g., 50% by weight aqueous potassium hydroxide) is diluted to the desired concentration with water. The non-aqueous solvent for the method is then added with agitation under otherwise ambient conditions. In one embodiment, a solvent for the reaction can be a nitrile, ether, alcohol, amide, ketone, sulfoxide, phosphate ester, or mixtures thereof. In another embodiment, the solvent is selected from the group consisting of acetonitrile, propionitrile, butyronitrile, methyl glutaronitrile, adiponitrile, benzonitrile, ethylene carbonate, propylene carbonate, ethanol, methanol, propanol, isopropanol, butanol, methyl ethyl ketone, methyl isoamyl ketone, diisobutyl ketone, anisole, 2-methyltetrahydrofuran, tetrahydrofuran, dioxane, diglyme, triglyme, tetraglyme, N,N-dimethyl formamide, N,N-dimethyl acetamide, N-methyl pyrrolidinone, sulfolane, dimethyl sulfoxide, perfluoro-N-methyl morpholine, perfluorotetrahydrofuran, and mixtures thereof. Preferred solvents include acetonitrile, adiponitrile, 2-methyl tetrahydrofuran, tetrahydrofuran, dioxane, diglyme, and tetraglyme.

As used herein, phase transfer catalyst is intended to mean a substance that facilitates the transfer of ionic compounds into an organic phase from an aqueous phase or from a solid phase. The phase transfer catalyst facilitates the reaction of these dissimilar and incompatible components. While various phase transfer catalysts may function in different ways, their mechanism of action is not determinative of their utility in the reaction provided that the phase transfer catalyst facilitates the dehydrofluorination reaction.

The phase transfer catalyst is selected from the group consisting of crown ethers, onium salts, cryptands, polyalkylene glycols, and mixture thereof.

In one embodiment, the base need not be highly soluble in the solvent. An amount of a phase transfer catalyst may be added to the solvent for the reaction in quantities that improve the solubility of the base therein. In one embodiment, the amount of phase transfer catalyst used will be from about 0.001 to about 10 mole percent based on the total amount of base present. In another embodiment, the amount of phase transfer catalyst used will be from about 0.01 to about 5 mole percent based on the total amount of base present. In yet another embodiment, the amount of phase transfer catalyst used will be from about 0.05 to about 5 mole percent based on the total amount of base present. In one embodiment of the invention, an aqueous or inorganic phase is present as a consequence of the base and an organic phase is present as a result of the HFO-1234yf and the non-aqueous solvent.

In some embodiments, the phase transfer catalyst can be ionic or neutral. In one embodiment, the phase transfer catalyst is selected from the group consisting of crown ethers, onium salts, cryptands and polyalkylene glycols and mixtures and derivatives thereof.

Crown ethers are cyclic molecules in which ether groups are connected by dimethylene linkages; the compounds form a molecular structure that is believed to be capable of "receiving" or holding the alkali metal ion of the hydroxide and to thereby facilitate the reaction. In some embodiments, it is preferred to match certain crown ether phase transfer catalysts with certain bases used in the basic aqueous solutions. In one embodiment, crown ethers include 18-crown-6, is used in combination with potassium hydroxide basic aqueous solution; 15-crown-5, is used in combination with sodium hydroxide basic aqueous solution; 12-crown-4, is used in combination with lithium hydroxide basic aqueous solution. Derivatives of the above crown ethers are also useful, e.g., dibenzo-18-crown-6, dicyclohexano-18-crown-6, and dibenzo-24-crown-8 as well as 12-crown-4. Other polyethers particularly useful in combination with basic aqueous solution made from alkali metal compounds, and especially for lithium, are described in U.S. Pat. No. 4,560,759 the disclosure of which is herein incorporated by reference. Other compounds analogous to the crown ethers and useful for the same purpose are compounds which differ by the replacement of one or more of the oxygen atoms by other kinds of donor atoms, particularly N or S, such as hexamethyl-[14]-4,11-diene$N_4$.

In some embodiments, onium salts include quaternary phosphonium salts and quaternary ammonium salts that may be used as the phase transfer catalyst in the process of the present invention; such compounds can be represented by the following formulas II and III:

$$R^1R^2R^3R^4P^{(+)}X'^{(-)} \qquad (II)$$

$$R^1R^2R^3R^4N^{(+)}X'^{(-)} \qquad (III)$$

wherein each of $R^1$, $R^2$, $R^3$ and $R^4$, which may be the same or different, is an alkyl group, an aryl group or an aralkyl group, and X' is selected from the group consisting of F, Cl, Br, I, OH, $CO_3$, $HCO_3$, $SO_4$, $HSO_4$, $H_2PO_4$, $HPO_4$ and $PO_4$. Specific examples of these compounds include tetramethylammonium chloride, tetramethylammonium bromide, benzyltriethylammonium chloride, methyltrioctylammonium chloride (a quaternary ammonium salt sold under the trademark Aliquat™ 336), tetra-n-butylammonium chloride, tetra-n-butylammonium bromide, tetra-n-butylammonium hydrogen sulfate, tetra-n-butylphosphonium chloride, tetraphenylphosphonium bromide, tetraphenylphosphonium chloride, triphenylmethylphosphonium bromide and triphenylmethylphosphonium chloride. In one embodiment, benzyltriethylammonium chloride is used under strongly basic conditions. Other useful compounds within this class of compounds include those exhibiting high temperature stabilities (e.g., up to about 200° C.) including 4-dialkylaminopyridinium salts, tetraphenylarsonium chloride, bis[tris(dimethylamino)phosphine]iminium chloride, and tetratris[tris(dimethylamino)phosphinimino]phosphonium chloride; the latter two compounds are also reported to be stable in the presence of hot, concentrated sodium hydroxide and, therefore, can be particularly useful.

In other embodiments, cryptands are another class of compounds useful in the reaction as phase transfer catalysts. These are three-dimensional polymacrocyclic chelating agents that are formed by joining bridgehead structures with chains that contain properly spaced donor atoms. For example, bicyclic molecules that result from joining nitrogen bridgeheads with chains of ($-OCH_2CH_2-$) groups as in 2.2.2-cryptand (4,7,13,16,21,24-hexaoxa-1,10-diazabicyclo-(8.8.8)hexacosane; available under the brand name Cryptand™ 222 and the trademark Kryptofix® 222). The donor atoms of the bridges may all be O, N, or S, or the compounds may be mixed donor macrocycles in which the bridge strands contain combinations of such donor atoms.

In some embodiments, polyalkylene glycol ethers are useful as phase transfer catalysts. In some embodiments, the polyalkylene glycol ethers can be represented by the formula:

$$R^6O(R^5O)_tR^7 \qquad (IV)$$

wherein $R^5$ is an alkylene group containing two or more carbon atoms, each of $R^6$ and $R^7$, which may be the same or different, is a hydrogen atom, an alkyl group, an aryl group or, an aralkyl group, and t is an integer of at least 2. Such compounds include, for example glycols such as diethylene glycol, triethylene glycol, tetraethylene glycol, pentaethylene glycol, hexaethylene glycol, diisopropylene glycol, dipropylene glycol, tripropylene glycol, tetrapropylene glycol and tetramethylene glycol, and monoalkyl ethers such as monomethyl, monoethyl, monopropyl and monobutyl ethers of such glycols, dialkyl ethers such as tetraethylene glycol dimethyl ether and pentaethylene glycol dimethyl ether, phenyl ethers, benzyl ethers, and polyalkylene glycols such as polyethylene glycol (average molecular weight about 300) dimethyl ether, polyethylene glycol (average molecular weight about 300) dibutyl ether, and polyethylene glycol (average molecular weight about 400) dimethyl ether, and ethoxylated furfurylalcohol. Among them, compounds wherein both R—$^6$ and R—$^7$ are alkyl groups, aryl groups or aralkyl groups are preferred.

Combinations and mixtures of the above described phase transfer catalysts from within one of the groups may also be useful as well as combinations or mixtures of two or more phase transfer catalysts selected from more than one group, for example, crown ethers and oniums, or from more than two of the groups, e.g., quaternary phosphonium salts and quaternary ammonium salts, and crown ethers and polyalkylene glycol ethers.

In one embodiment, the dehydrofluorination is conducted within a temperature range at which the $CF_3CHFCH_2F$ will dehydrofluorinate. In one embodiment, such temperatures can be from about 5° C. to about 150° C. In another embodiment, the reaction is conducted in the range of from about 10° C. to about 110° C. In yet another embodiment, the reaction is carried out in the range of from about 15° C. to about 90° C. The reaction pressure is not critical. The reaction can be conducted at atmospheric pressure, super-atmospheric pressure, or under reduced pressure. In one embodiment, the reaction is carried out at atmospheric pressure.

The dehydrofluorination reactions of this invention may be carried out in either a batch or a continuous mode. In some embodiments, the dehydrofluorination process is carried out in batch mode and in other embodiments, the dehydrofluorination continuous mode. In one embodiment, in the batch mode, the above described components are combined in a suitable vessel for a time sufficient to convert at least a portion of the HFC-245eb to HFO-1234yf and then the HFO-1234yf is recovered from the reaction mixture.

In another embodiment, in a continuous mode of operation, the reaction vessel is charged with the basic aqueous solution, non-aqueous, non-alcoholic solvent, and phase transfer catalyst; the HFC-245eb is then fed to the reactor. The reaction vessel is fitted with a condenser cooled to a temperature sufficient to reflux the HFC-245eb, but permit the HFO-1234yf to exit the reaction vessel and collect in an appropriate vessel such as cold trap.

Products formed by liquid phase dehydrofluorination comprise HF, HFO-1234yf, and, if HFC-254eb is present in the feed mixture, HFO-1243zf. In one embodiment, the HFO-1234yf is typically separated from the lower boiling products and higher boiling products by conventional means (e.g., distillation).

Dehydrofluorination of HFC-245eb may also produce HFO-1234ze (Z- and/or E-isomers) as an additional compound, under the same conditions, as described herein, used to produce HFO-1234yf from HFC-245eb. Higher temperatures have been found to produce higher levels of HFO-1234ze. This reaction is also shown in FIG. 1.

Hydrogenation of HFO-1234ze may produce HFC-254fb as an additional compound, under typical conditions for hydrogenation, as described in International Patent Application Publication WO2008/030440 A2. Generally, HFO-1234ze is added with hydrogen to a reaction vessel containing a hydrogenation catalyst, such as palladium or supported palladium, wherein the support may be alumina, aluminum fluoride, or carbon, as well as other hydrogenation catalysts. The reaction may be carried out at temperatures from about 50° C. to about 300° C. with a contact time of about 5 to about 100 seconds. The molar ratio of hydrogen to HFO-1234ze may be anywhere from about 1.5:1 to about 25:1. This reaction is shown in FIG. 1.

Hydrogenation of the product HFO-1234yf may produce HFC-254eb as an additional compound, as shown in FIG. 1, under the same conditions as described above for the hydrogenation of HFO-1234ze to HFC-254fb.

Dehydrofluorination of the HFC-254eb or HFC-254fb may produce HFO-1243zf as an additional compound, as shown in FIG. 1, under the same conditions as described herein for the dehydrofluorination of HFC-245eb to produce HFO-1234yf.

EXAMPLES

General Procedure for Product Analysis

The following general procedure is illustrative of the method used for analyzing the products of fluorination reactions. Part of the total reactor effluent was sampled on-line for organic product analysis using a gas chromatograph equipped with a mass selective detector (GC/MS). The gas chromatography utilized a 20 ft. (6.1 m) long×⅛ in. (0.32 cm) diameter tube containing a perfluorinated polyether sold under the trademark Krytox® by E.I. du Pont de Nemours and Company ("DuPont" of Wilmington, Del.) on an inert carbon support. The helium flow was 30 mL/min ($5.0 \times 10^{-7}$ m$^3$/sec). Gas chromatographic conditions were 60° C. for an initial hold period of three minutes followed by temperature programming to 200° C. at a rate of 6° C./minute.
Legend
23 is $CHF_3$
1132a is $CH_2=CF_2$
1225zc is $CF_3CH=CF_2$
1234yf is $CF_3CF=CH_2$
E- and Z-1234ze are E- and Z—$CF_3CH=CHF$
245eb is $CF_3CHFCH_2F$ Preparation of Fluorided Alumina Catalyst A Hastelloy® tube (1" OD×0.854 ID×10"L) was filled with 25 cc (16.68 grams) gamma-alumina ground to 12-20 mesh. The packed portion of the reactor was heated by a 5.0"×1" ceramic band heater clamped to the outside of the reactor. A thermocouple, positioned between the reactor wall and the heater, measured the reactor temperature. The catalyst was dried by heating at 200° C. overnight under a nitrogen flow of 50 sccm ($8.33 \times 10^{-7}$ m$^3$/s). The nitrogen flow was then reduced to 5 sccm ($8.33 \times 10^{-8}$ m$^3$/s) and a flow of 20 sccm ($3.33 \times 10$-7 m$^3$/s) CFC-12 ($CF_2Cl_2$) started and maintained for 60 minutes. The temperature was raised to 325° C. and held at this temperature for a further 60 minutes. The CFC-12 flow stopped and the reactor temperature raised to 400° C. under a flow of 50 sccm ($8.33 \times 10^{-7}$ m$^3$/s) of nitrogen and held at this temperature for an additional 60 minutes. The reactor was then brought to the desired operating temperature.

Example 1

Vapor Phase Dehydrofluorination of HFC-245eb to HFO-1234yf with Fluorided Alumina Catalyst To the reactor containing the fluorided alumina catalyst prepared as above was fed a vapor of HFC-245eb and nitrogen at various reactor temperatures. The nitrogen to HFC-245eb ratio was 0.67:1 and the contact time was 36 seconds for the first four analyses. For the fifth analysis, the nitrogen to HFC-245eb ratio was 1:1 and the contact time was 90 seconds. The product leaving the reactor was analyzed by GC/MS and the results in mole % are summarized in Table 2.

TABLE 2

| Reactor T, ° C. | 1234yf | E-1234ze | Z-1234ze | 245eb |
|---|---|---|---|---|
| 200 | ND | ND | ND | 99.9 |
| 300 | 14.3 | 3.6 | 0.8 | 81.2 |
| 350 | 28.2 | 9.5 | 2.3 | 60.0 |
| 400 | 45.4 | 18.9 | 4.4 | 31.3 |
| 400 | 52.0 | 22.0 | 5.4 | 20.4 |

ND = Not detected

Example 2

Pyrolysis of HFC-245eb

The reactor was a 9.5 inch (24.1 cm) long×0.50 inch (1.3 cm) outer diameter×0.35 inch (0.89 cm) inner diameter tubing with a wall thickness of 0.15 inch (3.8 mm) containing an internal gold lining. The thickness of the gold lining was 0.03 inch (0.08 cm). The reactor was heated with a ceramic band heater 5.7 inch long (14.5 cm)×1 inch outer diameter (2.5 cm) clamped to the outside. A dual control thermocouple, centered in the middle of the band heater between the outside of the reactor and the inside of the band heater was used to control and measure reactor temperature. To the reactor heated to various operating temperatures was fed 5 sccm ($8.33 \times 10^{-8}$ m$^3$/s) nitrogen and 2.37 mL per hour of liquid HFC-245eb that was vaporized before entering the reactor. The contact time was 60 seconds for all runs. The reactor effluent was analyzed by an in-line GC/MS. The product analysis in mole %, at various operating temperatures is summarized in Table 3.

TABLE 3

| Temp° C. | Unknown | 23 | 1132a | 1234yf | E-1234ze | 1225ye | Z-1234ze | 245eb |
|---|---|---|---|---|---|---|---|---|
| 600 | 0.5 | 0.8 | 0.1 | 3.1 | 1.0 | ND | 0.2 | 94.3 |
| 650 | 1.9 | 4.7 | 1.0 | 5.9 | 2.3 | 0.3 | 0.8 | 83.1 |

TABLE 3-continued

| Temp° C. | Unknown | 23 | 1132a | 1234yf | E-1234ze | 1225ye | Z-1234ze | 245eb |
|---|---|---|---|---|---|---|---|---|
| 700 | 4.3 | 17.4 | 5.1 | 16.7 | 8.5 | 1.8 | 3.7 | 42.5 |
| 750 | 7.7 | 24.6 | 7.9 | 28.0 | 14.8 | 3.4 | 6.6 | 6.9 |

ND = non-detectable

Example 3

Liquid Phase Dehydrofluorination of HFC-245eb to HFC-1234yf

A three neck, 2 liter flask was equipped with a water ice condenser, thermocouple, and over-head stirrer. The effluent of the condenser was passed through a $CaSO_4$ drier and then through activated molecular sieves and a stainless steel trap with dip tube immersed in dry ice/acetone. An oil bubbler made of perfluorinated polyether sold under the trademark Krytox® by DuPont (Wilmington, Del.) the exit of the stainless steel trap prevented contamination of the trapped product by moisture.

The flask was charged with water (736 mL), tetrahydrofuran (200 mL), KOH pellets (180 grams, 3.21 mol), and methyltrioctylammonium chloride, a quaternary ammonium salt sold under the trademark Aliquat™ 336 (3.13 grams, $7.74 \times 10^{-3}$ mol) that functions as a phase transfer catalyst. While vigorously stirring, $CF_3CHFCH_2F$ (HFC-245eb) was added at a rate of about 100 sccm. The pH of the basic aqueous solution was about 13. Two phases were present in the flask. About 247 grams of crude product was collected containing 96.1% 1234yf, 0.5% Z-1234ze, 0.1% E-1234ze and 2.9% unreacted HFC-245eb. Very little exotherm was observed while feeding the HFC-245eb.

What is claimed is:

1. A composition comprising HFO-1234yf, HFO-1234ze, HFC-245eb, and HFC-245cb; wherein said composition contains less than about 1 weight percent total of HFO-1234ze, HFC-245eb, and HFC-245cb.

2. The composition of claim 1 wherein the composition comprises E-HFO-1234ze and Z-HFO-1234ze.

* * * * *